United States Patent [19]

Meijs et al.

[11] Patent Number: 5,393,858
[45] Date of Patent: Feb. 28, 1995

[54] POLYURETHANE OR POLYURETHANE-UREA ELASTOMERIC COMPOSITIONS

[75] Inventors: Gordon F. Meijs, Murrumbeena; Ezio Rizzardo, Wheelers Hills; Arthur Brandwood, Alexandria; Pathiraja Gunatillake, Mulgrave; Klaus H. Schindhelm, Cherrybrook, all of Australia

[73] Assignees: Commonwealth Scientific and Industrial Research Organisation, Campbell; Unisearch Limited, Kensington, both of Australia

[21] Appl. No.: 962,799

[22] PCT Filed: Jun. 26, 1991

[86] PCT No.: PCT/AU91/00270

§ 371 Date: Feb. 23, 1993

§ 102(e) Date: Feb. 23, 1993

[87] PCT Pub. No.: WO92/00338

PCT Pub. Date: Jan. 9, 1992

[30] Foreign Application Priority Data

Jun. 26, 1990 [AU] Australia .................. PK 0817/90

[51] Int. Cl.$^6$ .................................................. C08G 18/30
[52] U.S. Cl. ................................. 528/61; 528/59; 528/76
[58] Field of Search ............................ 528/61, 58, 76

[56] References Cited

U.S. PATENT DOCUMENTS 3,252,943  5/1966  Dankert ........................... 528/69

FOREIGN PATENT DOCUMENTS 0136396  4/1985  European Pat. Off. .
0295640  12/1988  European Pat. Off. .
2008761  1/1970  France .
1495209  1/1969  Germany .
60-252617  5/1984  Japan .
2292318  12/1990  Japan .
3-50225  3/1991  Japan .

*Primary Examiner*—Maurice J. Welsh
*Attorney, Agent, or Firm*—Bacon & Thomas

[57] ABSTRACT

A polyurethane or polyurethane-urea elastomeric composition, characterized in that the composition is a reaction product of:
(A) a soft segment macrodiol which is either:
  (i) a homopolymer represented by formula I, $$\text{HO}-[(\text{CH}_2)_n\text{O}]_m-\text{H} \qquad \text{I}$$

wherein n represents an integer greater than 5 and less than 13, m is a number such that the number average molecular weight of the compound of formula I falls in the range from 218 to 5000 and optionally at least one hydrogen atom represented in formula I is substituted by a $C_1$ to $C_3$ alkyl group or a halogen atom;
  (ii) a copolymer containing at least 25% by mass of repeating units $-(CH_2)_n\text{O}-$ wherein n is as defined in formula I above; or
  (iii) mixture of macrodiols comprising greater than 10% of a macrodiol as defined in formula I above;
(B) an aliphatic or aromatic diisocyanate known in the art of polyurethane manufacture; and
(C) optionally a chain extender.

A biomaterial and a medical device which are composed wholly or partly of the polyurethane or polyurethane-urea elastomeric composition are also described.

19 Claims, No Drawings

POLYURETHANE OR POLYURETHANE-UREA ELASTOMERIC COMPOSITIONS

The invention relates to polyurethane or polyurethane-urea elastomeric compositions which are particularly suitable for use in devices that contact living tissue or bodily fluids.

The applications of polyurethane elastomers are limited by their susceptibility to degradation, particularly hydrolysis and oxidation. For example, degradation problems have arisen with artificial leathers, shoe soles and cable sheathing. This problem has been partially overcome by the use of polyether macrodiols. The problem is particularly acute in biomedical applications where because of their good mechanical performance (e.g. high tensile strength, good tear and abrasion resistance), inherent biocompatibility and nonthrombogenicity, polyurethanes are the materials of choice for many applications and have found use in pacemakers leads, various types of catheters, implantable prostheses, cardiac assist devices, heart valves, sutures, and vascular grafts, as well as in extra-corporeal blood contacting applications.

Polyurethane elastomers are usually prepared by reacting excess diisocyanate with a polyol "soft segment" to form a prepolymer having terminally reactive isocyanate groups, which is then reacted with a diol or diamine chain extender. Although the diisocyanate plays an important role, many of the properties associated with the polyurethane elastomer are derived from the soft segment portion of the chain. The soft segments of most commercial polyurethane elastomers are derived from polyether macrodiols, for example poly(ethylene oxide), poly(propylene oxide) and poly(tetramethylene oxide) and polyester macrodiols (poly(ethylene adipate) and polycaprolactone glycols. Polyurethanes that have polyether soft segments have better resistance to hydrolysis than those with polyester soft segments and are preferred as biomaterials. The most widely accepted commercial medical-grade polyurethanes are Pellethane (Registered Trade Mark) and Biomer (Registered Trade Mark), although Tecoflex (Registered Trade Mark), Vialon (Registered Trade Mark) and Mitrathane (Registered Trade Mark) have found some acceptance. These materials all have in common the use of poly(tetramethylene oxide) as the macrodiol soft segment. S. Gogolewski in *Colloid and Polymer Science*, volume 267, pp 757–785 (1989) summarizes the prior art commercial and experimental biomedical polyurethanes which have been disclosed. There are no reports of biomedical polyurethanes having the composition described below.

The biostability of polyurethanes is reviewed by Michael Szycher, a recognized leader in the field, in *Journal of Biomaterials Applications*, volume 3, pp 297–402 (October, 19&8). Degradation can be manifested in terms of surface or deep cracking, stiffening, erosion, or the deterioration of mechanical properties, such as flex life. The deterioration ultimately leads to failure of the device. Degradation can also cause the leaching of cytotoxic agents, resulting in tissue necrosis or in some cases, the formation of tumors. The inadequate biostability of polyurethanes is generally recognised as a severe limitation to the successful development of long term artificial hearts and synthetic polyurethane small bore vascular grafts.

The biologically-induced degradation of polyurethanes has been attributed to several factors and some of these are summarized in the review by Michael Szycher cited above. Although there is still some controversy, it is widely held that the following mechanisms of degradation are important:
a) environmental stress cracking
b) oxidation;
c) hydrolysis;
d) calcification; and
e) other metal ion promoted degradation (e.g. silver, cobalt).

Other agents (e.g. fungi) have also been implicated by some workers. Of these degradative pathways, environmental stress cracking is arguably the most complex and depends on a combination of a chemical agent and either residual internal stress (e.g. from processing), or externally applied stress (e.g. from flexing of an implant during use). Calcification has been reviewed by R. J. Thoma and coworkers in *Journal of Biomaterials Applications*, volume 3, pp 180–206 (October, 1988) and is a problem in certain applications, such as in the artificial heart and in heart valve replacements. The soft segment has been implicated as a site of initial complexation with metal ions.

The present invention provides a polyurethane or polyurethane-urea elastomeric composition which has improved durability in hostile environments, particularly as a biomaterial. More specifically, the composition of the invention displays a surprisingly enhanced resistance to in vivo degradation, oxidation and hydrolysis while maintaining good mechanical properties and blood and tissue comparability making the composition suitable for the construction of medical devices, implants and extra corporeal devices as discussed above. The biostability of the composition of the invention is greater than that of the commercially accepted polyurethanes Pellethane 2363-80A (Registered Trade Mark) and Biomer (Registered Trade Mark). Such improvements are a consequence of the actual polyurethane or polyurethane-urea elastomer composition itself, integral to which is the inclusion of a soft segment defined below.

The polyurethane or polyurethane-urea elastomeric composition of the invention may be used as a biomaterial. The term "biomaterial" as used herein refers to a material which is used in situations where it comes into intimate contact with the cells and body fluids of living animals or humans.

According to the present invention there is provided a polyurethane or polyurethane-urea elastomeric composition, characterized in that the composition is a reaction product of:

(A) a soft segment macrodiol which is either:
(i) a homopolymer represented by formula I,

$$HO-[(CH_2)_nO]_m-H \qquad I$$

wherein n represents an integer greater than 5 and less than 13, m is a number such that the number average molecular weight of the compound of formula I falls in the range from 218 to 5000 and optionally at least one hydrogen atom represented in formula I is substituted by a $C_1$ to $C_3$ alkyl group or a halogen atom, such as fluorine;

(ii) a copolymer containing at least 25% by mass of repeating units $-(CH_2)_nO-$ wherein n is as defined in formula I above; or (iii) a mixture of macrodiols comprising greater than 10% of a macrodiol as defined in formula I above;

(B) an aliphatic or aromatic diisocyanate known in the art of polyurethane manufacture; and (C) optionally a chain mender.

Further according to the present invention there is provided a polyurethane or polyurethane-urea elastomeric composition for use as a biomaterial.

Preferably, the aliphatic or aromatic diisocyanate (B) is selected from 4,4'-diphenylmethane diisocyanate (MDI),
methylene bis(cyclohexyl) diisocyanate ($H_{12}MDI$),
p-phenylene diisocyanate (p-PDI),
trans-cyclohexane- 1,4-diisocyanate (CHDI),
1,6-diisocyanatohexane (DICH),
2,4-toluene diisocyanate (2,4-TDI),

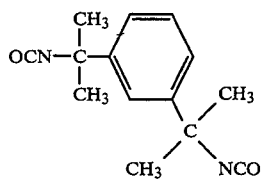

II and para-tetramethylxylene diisocyanate (p-TMXDI) represented by the formula III,

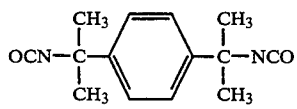

III

The chain extender (C) is preferably selected from
1,4-butanediol (BDO),
1,6-hexanediol (HDO),
1,2-ethytenediamine (EDA),
1,6-hexanediamine (HDA) and
1,2-propanediamine (1,2-PDA).

The composition of the invention may be prepared by any suitable known technique, using either one-step or two-step procedures. Preferably a two-step solution polymerization method is used employing solvents such as dimethyl acetamide and dimethylformamide (DMF). It will be appreciated however that one step procedures and procedures that do not employ a reaction solvent which are well known in the art are also applicable. In addition, small mounts of cross-linking agents, preferably <5%, may be incorporated in the composition. Other materials, such as polysiloxane-containing polymers or oligomers may also be blended with the composition. In addition, the composition of the invention may optionally contain reaction catalysts, antioxidants, stabilizers and processing aids.

The soft segments (A) may be prepared by acid catalysed condensation of the appropriate low molecular weight diol or by acid catalysed ring opening reactions of cyclic ethers. The preparation of these materials may be accomplished by the method outlined by K. Yamamoto and H. Fujita in *Polymer*, volume 7, pp 557–562 (1966) or by the procedure given below, in which poly(-hexamethylene oxide) was prepared by the acid catalysed condensation of the corresponding monomer diol, 1,6-hexamethylene diol.

In another aspect of the present invention there is provided a biomaterial which is wholly or partly composed of the polyurethane or polyurethane-urea elastomeric composition described above.

In a further aspect of the present invention there is provided a medical device, article or implant which composed wholly or partly of the polyurethane or polyurethane-urea elastomeric composition described above.

Preferably the biomaterial, medical device, article or implant is composed of a material comprising not less than 10% of the polyurethane or polyurethane-urea elastomeric composition described above.

The medical device, article or implant may be produced by any suitable known technique, such as extrusion, solvent casting and injection molding.

PROCEDURE 1

1,6-Hexamethylene diol (200 g) was placed in a 500 ml round bottom flask and heated under vacuum (0.1 torr) at 100° C. for 1 hour. The flask was cooled to 50° C., and fitted with a nitrogen bleed, Dean-Stark tube and a condenser. Concentrated sulphuric acid (2.2 ml) was added dropwise with stirring, and the reaction mixture was heated at 170° C. for three hours under a stream of dry nitrogen. The flask was then connected to a vacuum pump, and heating continued at the same temperature under a vacuum of 0.1 torr. Polymers with different molecular weights were obtained by varying the interval of this heating process. The sulphuric acid catalyst was removed by treating the polymerized reaction mixture with a saturated solution of calcium hydroxide. The product was further purified by recrystallization with a 70/30 (v/v) mixture of ethanol and water. The solid product isolated by filtration was dried in a vacuum oven at 45 C. for 48 hours. The same experimental procedure was followed for the preparation of poly(octamethylene oxide) and poly(decamethylene oxide).

The invention is further illustrated by the following non-limiting examples.

EXAMPLE 1

Poly(octamethylene oxide) was placed,in a 500 ml round bottom flask and heated at 100 C. under vacuum (0.1 torr) for 15 hours to remove volatiles. The dried poly(octamethylene oxide) (MW 870) (60.67 g, 0.069 mole) was placed in a 500 ml round bottom flask, fitted with a nitrogen bleed, magnetic stirrer, condenser, and drying tube. m-TMXDI (43.59 g, 0.178 mole), DMF (105.0 g), and dibutyltin dilaurate (1.72 ml of a 1.0% w/v solution in toluene) were also placed in the flask and the resulting mixture was stirred at 100 C. under a slow stream of dry nitrogen for 4 hours. The isocyanate content of the prepolymer solution was 3.0% as determined by ASTM method D 1638-74. The prepolymer (191.2 g) was then diluted to 25% w/v by adding anhydrous DMF and was transferred to a 1.0 L round bottom flask fitted with a nitrogen bleed, mechanical stirrer, condenser and a drying tube. Hexamethylenediamine (7.931 g) was added as a 10% w/v solution in DMF to the reaction mixture under dry nitrogen at room temperature over a period of 15 mins. The reaction mixture was stirred at room temperature for 1 hour followed by 3 hours at 100 C. The resulting polymer solution was then diluted to 7% w/v and precipitated into deionized water (4 L). The precipitated polymer was stirred in fresh deionized water for 15 hours, filtered and dried in a vacuum oven at 55 C. for 72 hours. The dried polymer was melt pressed at 120 C. (8 tons)

into 1 mm thick sheets and tested for mechanical properties. The results are shown in Table 1.

This material showed enhanced biostability compared with Pellethane 2363-80A {Registered Trade Mark) and Biomer (Registered Trade Mark) on subcutaneous implantation in an unstressed configuration in sheep (see Example 10 for details of that method). It also displayed good tissue compatibility as shown by examining the tissue surrounding the specimen after explant (6 months). There was a less active interface with fewer macrophages, giant cells and granulation tissue than Biomer (Registered Trade Mark) and the material gave a response similar to Tecoflex EG80A (Registered Trade Mark).

EXAMPLE 2

The procedure described in Example 1 was followed, except that poly(hexamethylene oxide) with a number average molecular weight of 1190 was used. The prepolymer was produced by mixing:

(a) 45.17 g (0.038 mole) of poly(hexamethylene oxide), having a number average molecular weight of 1190, with:

(b) 67.78 g of DMF; with (c) 22.61 g (0.093 mole) of m-TMXDI; in the presence of (d) 0.015% by weight, based on the weight of [(a)+(c)], of dibutyltin dilaurate.

The isocyanate content of the prepolymer was 3.35%. The prepolymer solution (57.15 g) was diluted with DMF to 25%, and chain extended with 1,6-hexamethylenediamine (2.648 g), using the procedure in Example 1. The dried polymer was melt pressed at 160 C. into 1 mm thick sheets and its mechanical properties were evaluated. The results are shown in Table 1.

EXAMPLE 3

Poly(octamethylene oxide) was placed in a 500 mL round bottom flask and heated at 100 C. under vacuum (0.1 torr) for 15 hours to remove volatiles. The dried poly(octamethylene oxide) (MW 1172, 32.51 g, 0.028 mole) was placed in a 100 mL addition funnel along with DMF (25.0 g). A 500 mL round bottom flask was fitted with a nitrogen bleed, magnetic stirrer and a condenser, and a drying tube. m-TMXDI (16.94 g, 0.069 mole), DMF (48.84 g), and dibutyltin dilaurate (0.8 ml of a 0.5% w/v solution in toluene) were placed in the flask and heated to 100 C. Poly(octamethylene oxide) solution was added to the flask over a period of 30 mins under a slow stream of dry nitrogen. Upon completion of the addition, the resulting polymer was heated for 4 hours at 100 C. The isocyanate content of the prepolymer solution was 3.15% as determined by ASTM method D 1638-74. The prepolymer (51.07 g) was diluted to 2.5% by adding DMF and placed in a 500 mL round bottom flask fitted with a nitrogen bleed, mechanical stirrer, condenser and a drying tube. Hexamethylenediamine (2.222 g) was added as a 10% solution in DMF to the reaction mixture over a period of 15 mins. The reaction mixture was stirred at room temperature for 1 hour followed by 4 hours at 100 C. The resulting polymer solution was diluted to 10% and precipitated into deionized water (4 L). The precipitated polymer was stirred in fresh deionized water for 15 hours, filtered and dried in a vacuum oven at 55 C. for 72 hours. The dried polymer was melt pressed at 120 C. into 1 mm thick sheets and its mechanicla properties were evaluated. The results are shown in Table 1.

TABLE 1

| | Example 1 | Example 2 | Example 3 |
|---|---|---|---|
| Hardness, Shore A | 86 | 85 | — |
| Stress at 50% elongation, MPa | — | 4.8 | 4.7 |
| Stress at 100% elongation, MPa | 12.5 | 63 | 5.6 |
| Stress at 300% elongation, MPa | — | 9.1 | 8.3 |
| Tensile strength, MPa | 23 | 26 | 23 |
| Elongation at break, % | 920 | 980 | 920 |
| Tensile set, % | 40 | 20 | 40 |
| Number Average MW (daltons) | 68,500 | 94,000 | 47,700 |
| Dispersity (Mw/Mn) | 1.49 | 2.04 | 1.71 |

EXAMPLE 4

Poly(hexamethylene oxide) (number average molecular weight of 650) was placed in a 500 mL round bottom flask and heated at 100 C. under vacuum (0.1 torr) for 15 hours to remove volatiles. The dried poly(hexamethylene oxide) (47.54 g, 0.073 mole) was placed in a 250 mL addition funnel along with anhydrous N,N-dimethylformamide [DMF] (50.0 g). A 500 mL round bottom flask was fitted with a nitrogen bleed, magnetic stirrer, condenser, and a drying tube. 4,4'-Diphenylmethane diisocyanate (45.48 g, 0.182 mole) and DMF (45.7 g) were placed in the flask and heated to 80 C. The poly(hexamethylene oxide) solution was added to the flask over a period of 30 rains under a slow stream of dry nitrogen. Upon completion of the addition, the resulting mixture was heated for 2 hours at 80 C. The isocyanate content of the prepolymer solution was 4.15% as determined by ASTM method D 1638-74. The prepolymer solution (91.75 g) was diluted to 25% w/v by adding anhydrous DMF and then placed in a 500 mL round bottom flask fitted with a nitrogen bleed mechanical stirrer, condenser and a drying tube. The catalyst, stannous octoate (0.015% w/w of total solids in the prepolymer), was added to the prepolymer solution. Chain extension of the prepolymer was carried out by adding a 10% w/v solution of 1,4-butanediol (4.037 g) in anhydrous DMF over a period of 30 rains to the prepolymer solution under dry nitrogen at room temperature. The reaction mixture was then heated for 2 hours at 80 C. The resulting polymer solution was cooled and diluted to 7% w/v and precipitated in deionized water (4 L). The precipitated polymer was stirred in fresh deionized water for 15 hours, filtered, and dried in a vacuum oven at 55 C. for 72 hours. The dried polymer was melt pressed at 140 C. (8 tons) into 1 mm thick sheets and its mechanical properties were evaluated. The results obtained are shown in Table 2. The polymer exhibited characteristics expected of a degradation resistant material. For example, the material exhibited good hydrolytic and oxidative stability when tested by boiling weighted dumbells for 24 hours in 2M hydrochloric acid, in 2M sodium hydroxide and in 25% hydrogen peroxide. After washing with water and drying, the dumbells showed a 16%,9% and 19% decrease in ultimate stress respectively, whereas the corresponding decreases for Pellethane 2363-80A (Registered Trade Mark) were 47%, 23% and 62%.

The material, when implanted subcutaneously in sheep in both strained (3 month implant) and unstrained configurations (6 month implant), displayed a greater biostablility than either Pellethane 2363-80A (Registered Trade Mark) or Biomer (Registered Trade Mark) (see Example 10 and 11 for details of the test method). Microscopic examination of the tissue surrounding the implanted material showed a similar tissue response to that of Pellethane 2363-80A (Registered Trade Mark). The material was, however, significantly more histocompatible than Biomer (Registered Trade Mark). There was low to moderate capsule cellularity and fewer dilated capillaries. Giant cell activity was not observed and there was a smooth interface with some scattered macrophages. The material had similar haemocompatibility to Biomer (Registered Trade Mark) or Pellethane 2363-80A {Registered Trade Mark) as assayed by whole blood clotting time and platelet adhesion tests. The material was judged to be a suitable biomaterial.

TABLE 2

|  | Example 4 | Example 5 | Example 6 |
|---|---|---|---|
| Hardness, Shore A | 90 | 93 | — |
| Stress at 50% elongation,MPa | 9.1 | 8.3 | 4.0 |
| Stress at 100% elongation,MPa | 13.1 | 8.4 | 5.6 |
| Stress at 300% elongation,MPa | 18.3 | 10.8 | 10.5 |
| Tensile strength, MPa | 19 | 13 | 17 |
| Elongation at break, % | 390 | 560 | 460 |
| Tensile set, % | 30 | 260 | 32 |
| Mn (Number Average MW) (daltons) | 47,250 | 25,200 | — |
| Dispersity (Mw/Mn) | 2.13 | 1.88 | — |

EXAMPLE 5

Poly(octamethylene oxide) was placed in a 500 mL round bottom flask and heated at 100 C. under vacuum (0.1 torr) for 15 hours to remove volatiles. The dried poly(octamethylene oxide) (MW 1685) (40.02 g, 0.024 mole) was placed in a 500 ml round bottom flask fitted with a nitrogen bleed, magnetic stirrer, condenser, and a drying tube. A solution of MDI (14.87 g, 0.059 mole ) in anhydrous DMF (58.0 g) was added to the flask which was then heated at 90 C. under a slow stream of dry nitrogen for 2 hours. The isocyanate content of the prepolymer solution was 2.14% as determined by ASTM method D1638-74. The prepolymer (63.1 g) was then diluted to 25% w/v by adding anhydrous DMF and placed in a 500 ml round bottom flask fitted with a nitrogen bleed, mechanical stirrer, condenser and a drying tube. The chain extension was carried out with 1,4-butanediol in the presence of stannous octoate (0.015% by weight of total solids in prepolymer) by heating at 90 C. for 2 hours. The resulting polymer solution was diluted to 8% w/v and precipitated in deionized water (4 L). The precipitated polymer was stirred in fresh deionized water for 15 hours, filtered and dried in a vacuum oven at 55 C. for 72 hours. The dried polymer was melt pressed at 120 C. (8 tons) into 1 mm thick sheets and its tensile properties were measured. The results appear in Table 2. In in vitro testing the polymer exhibited stability characteristics expected of a material for long term implantation and showed good haemocompatibility as assayed by whole blood .clotting time and platelet adhesion tests. The material exhibited good hydrolytic and oxidative stability when tested by boiling for 24 hours in 2M hydrochloric acid, in 2M sodium hydroxide and in 25% sodium hypochlorite. The material showed a 21%, 4% and 22% decrease in ultimate tensile stress respectively, whereas the corresponding decreases for Pellethane 2363-80A (Registered Trade Mark) were 47%, 23% and 31%, after treatment.

The material showed enhanced biostability when compared with Pellethane 2363-80A (Registered Trade Mark) and Biomer (Registered Trade Mark), using the ovine implantation procedures described in Example 4 and in more detail in Examples 10 and 11.

EXAMPLE 6

A similar procedure to that described in Example 5 was used. However, in this example poly(decamethylene oxide) of number average molecular weight of 1270 was used as the macrodiol. The prepolymer was made by mixing:

(a) 36.24 g (0.029 mole) of poly(decamethylene oxide), having a number average molecular weight of 1270; with (b) 54.3 g of DMF and with (c) 17.88 g (0.071 mole) of MDI and then heating for 2 hours at 90 C. The NCO content of the prepolymer was 2.35%. The prepolymer solution (18.2 g) was diluted with DMF to 10% w/v, and chain extended with 1,4-butanediol (0.458 g) in the presence of stannous octoate (0.015% by weight of total solids in prepolymer) catalyst, using the procedure in Example 5, except the reaction was carried out for 1 hour at 90 C. The dried polymer was melt pressed at 160 C. (8 tons) into 1 mm thick sheets and tested for mechanical properties. The results are summarised in Table 2. The material was also shown to be readily extrudable. The polymer exhibited good stability. For example, the material exhibited good hydrolytic and oxidative stability when tested by refluxing for 24 hours in 2M hydrochloric acid, in 2M sodium hydroxide and in 25% sodium hypochlorite, respectively. The material showed a 0%, 15% and 7% decrease in ultimate stress respectively, whereas the corresponding decreases for Pellethane 2363-80A (Registered Trade Mark) were 47%, 23% and 31%. The material was more biostable than Pellethane 2363-80A (Registered Trade Mark) and Biomer (Registered Trade Mark), as evidenced by strained and unstrained ovine implantation tests as described in Examples 10 and 11. Whole blood clotting time and platelet adhesion tests also indicated that the material had good compatibility with blood.

EXAMPLE 7

A similar procedure to that described in Example 1 was used. However, in this example poly(decamethylene oxide) of number average molecular weight of 1270 was used as the macrodiol. The prepolymer was made by mixing:

(a) 43.9 g (0.035 mole) of poly(decamethylene oxide), having a number average molecular weight of 1270 with:

(b) 71.4 g of DMF (c) 21.15 g (0.087 mole) of m-TMXDI and (d) 0.015% by weight, based on the weight of [(a)+(c)] of dibutyltin. dilaurate and heating at 90 C. for 4 hours.

The NCO content of the prepolymer was 3.14%. The prepolymer solution (112.2 g) was diluted with DMF to 25% w/v, and chain extended with 1,6-hexanediamine (4.864 g) using the procedure in Example 1, except the reaction was carried out for 3 hours at 90 C. The dried polymer was melt pressed at 140 C. (8 tons) into 1 mm thick sheets and tested for mechanical properties. The results obtained are shown in Table 3.

The material had similar stability to Pellethane 2363-80A (Registered Trade Mark), but enhanced stability over Biomer (Registered Trade Mark), as measured by a test involving 6 month subcutaneous ovine implantation described in Example 10. The material displayed satisfactory tissue compatibility on histopathological examination, being similar to Biomer (Registered Trade Mark).

EXAMPLE 8

A similar procedure to that described in Example 4 was followed. However, 2,4-toluene diisocyanate [TDI] was used instead of MDI, and the reaction was carried out for 3 hours at 90 C. instead of 2 hours at 80 C. The prepolymer was made by mixing:

(a) 50.1 g (0.038 mole) of poly(hexamethylene oxide), having a number average molecular weight of 1320; with (b) 102.4 g of DMF and (c) 16.58 g (0.095 mole) of 2,4-TDI The NCO content of the prepolymer was 2.76%. The prepolymer solution (138.1 g) was diluted with DMF to 12% w/v, and chain extended with 1,2-ethylenediamine (2.725 g) in the presence of stannous octanoate (0.015% by weight of total solids in prepolymer) catalyst, using the procedure in Example 4, except that the reaction was carried out for 3 hours at 80 C. The dried polymer was melt pressed at 160 C. into 1 nun thick sheets and tested for mechanical properties. The results are shown in Table 3.

TABLE 3

|  | Example 7 | Example 8 | Example 9 |
|---|---|---|---|
| Hardness, Shore A | — | — | 90 |
| Stress at 100% elongation, MPa | 14.5 | 14.8 | 5.8 |
| Stress at 300% elongation, MPa | 18.8 | 17.3 | — |
| Tensile strength, MPa | 19.7 | 20.4 | 10.6 |
| Elongation at break, % | 320 | 420 | 490 |
| Tensile set, % | 85 | 48 | 15 |
| Mn (daltons) | — | 41,400 | 23,000 |
| Dispersity (Mw/Mn) | — | 1.66 | 1.86 |

The material showed improved biostability over Pellethane 2363-80A (Registered Trade Mark) or Biomer (Registered Trade Mark) when examined after subcutaneous implantation in sheep for 3 months in a stressed configuration (see Example 11 ). Examination of the surrounding tissue showed that the material displayed good histocompatability with a capsule thickness of 100–200 microns which was smaller than that from Biomer (Registered Trade Mark) and comparable with that from Pellethane 2363-80A (Registered Trade Mark).

EXAMPLE 9

A similar procedure to that described in Example 4 was followed. However, methylene bis(cyclohexyl) diisocyanate ($H_{12}$MDI) was used instead of MDI and the reaction was carried out for 4 hours at 90 C. The prepolymer was made by mixing:

(a) 35.75 g (0.055 mole) of poly(hexamethylene oxide), having a number average molecular weight of 650; with (b) 68.8 g of anhydrous DMF; with (c) 31.55 g (0.120 mole) of $H_{12}$MDI; in the presence of (d) 0.015% of the combined weight of [(a)+(c)] of dibutyltin dilaurate.

The NCO content of the prepolymer was 2.7%. The prepolymer solution (113.0 g) was diluted with DMF to 10% w/v, and chain extended with 1,4-butanediol (3.264 g), using the procedure in Example 4, except the reaction was carried out for 3 hours at 100 C. The dried polymer was melt pressed at 140 C. (8 tons) into 1 mm thick sheets and its tensile properties were evaluated. The results are shown in Table 3. When implanted for 6 months subcutaneously in sheep in an unstressed configuration, the material degraded to a similar extent as Biomer (Registered Trade Mark). Examination of the tissue surrounding the explanted material indicated a capsule of 100–200 microns thick, compared with that from Biomer (Registered Trade Mark) of 210–300 microns. The material also caused a less active interface with fewer macrophages and giant cells and a smaller mount of granulation tissue indicating improved histocompatibility.

EXAMPLE 10

Details of the six month ovine in vivo biostability test are given in this example.

Each of the novel materials in Table 4 was formed by melt pressing into sheets of 1 mm thickness. Similarly, sheets of similar thickness were prepared from Pellethane 2363-80A (Registered Trade Mark) and from Tecoflex EG-80A (Registered Trade Mark). Sheets of Biomer (Registered Trade Mark) of 1 mm thickness were prepared by solvent casting from a 30% w/v solution in N,N-dimethylacetamide in a nitrogen atmosphere.

TABLE 4

Polyurethanes assessed for biostability by using the unstressed ovine implant test

| polyurethane | di-isocyanate | macrodiol | macrodiol mol wt | chain extender |
|---|---|---|---|---|
| Example 1 | m-TMXDI | POMO | 850 | HDA |
| Example 4 | MDI | PHMO | 650 | BDO |
| Example 5 | MDI | POMO | 1685 | BDO |
| Example 6 | MDI | PDMO | 1270 | BDO |
| Example 7 | m-TMXDI | PDMO | 1270 | HDA |
| Example 8 | 2,4-TDI | PHMO | 1320 | EDA |
| Example 9 | $H_{12}$MDI | PHMO | 650 | BDO |
| Pellethane (Registered Trade Mark) 2363-80A | MDI | PTMO[a] | 1000 | BDO |
| Tecoflex (Registered Trade Mark) EG-80A | $H_{12}$MDI | PTMO[a] | — | — |
| Biomer (Registered Trade Mark) | MDI | PTMO[a] | 1000 | Primarily EDA |

[a]poly(tetramethylene oxide)

Specimens of size 35 mm by 10 mm were cut from these sheets. Materials were identified by means of a binary code punched into one end of each specimen. The specimens were sterilized with ethylene oxide and implanted into the subcutaneous adipose tissue in the dorsal thoraco-lumbar region of adult crossbred wether sheep.

After a period of six months, the specimens were retrieved. Attached tissue was carefully dissected away and the specimens were washed by soaking in 0.1M sodium hydroxide at ambient temperature for 2 days followed by rinsing in deionized water. The specimens were then dried in air and examined by scanning electron microscopy (SEM).

The specimens were ranked according to their surface structure as determined by SEM as follows:

| Rank | Criteria |
|---|---|
| 1 | The specimen surface was smooth. |
| 2 | Cracking or pitting was present around the coding holes only. The remainder of the surface was smooth. |
| 3 | Fine cracks or pits were present both at coding holes and elswhere over the specimen surface. |
| 4 | Coarse cracking or pitting was present around the holes only. Fine cracking or pitting was present elswhere. |
| 5 | Coarse cracking or pitting was present over the entire surface of the specimen. |
| 6 | The surface showed extensive deep cracking or pitting associated with loss of material from the surface. |

The rankings obtained by the materials listed in the examples of this invention were as follows.

TABLE 5

| Rank | Polyurethane |
|---|---|
| 1 | Example 5 |
| 1 | Example 6 |
| 2 | Example 4 |
| 2 | Example 1 |
| 3 | Pellethane 2363-80A (Registered Trade Mark) |
| 3 | Tecoflex EG-80A (Registered Trade Mark) |
| 3 | Example 7 |
| 4 | Biomer (Registered Trade Mark) |
| 4 | Example 8 |
| 5 | Example 9 |

Control specimens that were not implanted in sheep, but cleaned with sodium hydroxide in an identical manner to those which had been implanted and control specimens that were neither implanted nor cleaned were also examined by SEM. Both of these control groups showed no changes in surface structure and were ranked 1 in all cases.

These results show that the novel polyurethanes produced according to the present invention had good biostability. In particular, the polyurethanes prepared in Examples 1, 4, 5 and 6 showed a much greater stability than that of the commercially accepted polyurethanes Pellethane 2363-80A (Registered Trade Mark), Biomer (Registered Trade Mark), and Tecoflex EG-80A (Registered Trade Mark).

Histopathological assessment was carried out by examining the surrounding tissue capsules preserved from separate implanted samples with reference particularly to capsule cellularity, capsule thickness, vascularity, presence or absence of polymorphonucleated cells and multinucleated giant cells, and the mount of granulation tissue at the interface (macrophages, fibroblasts, and giant cells). The assessment of tissue response was judged by considering these factors as a whole using Biomer (Registered Trade Mark) and Pellethane 2363-80A (Registered Trade Mark) as reference materials.

EXAMPLE 11

Each of the materials listed in Table 6 (with the exception of Biomer (Registered Trade Mark)) was formed, by melt pressing, into sheets of 0.5 mm thickness. Sheets of Biomer (Registered Trade Mark) of 0.5 mm thickness were prepared by solvent casting under nitrogen. The polyurethanes tested are listed in Table 5.

TABLE 6

| polyurethane | di-isocyanate | macrodiol | macrodiol mol wt | chain extender |
|---|---|---|---|---|
| Example 4 | MDI | PHMO | 650 | BDO |
| Example 5 | MDI | POMO | 1685 | BDO |
| Example 6 | MDI | PDMO | 1270 | BDO |
| Example 8 | 2,4-TDI | PHMO | 1320 | EDA |
| Pellethane 2363-80A (Registered Trade Mark) | MDI | PTMO[a] | 1000 | BDO |
| Tecoflex EG-80A (Registered Trade Mark) | $H_{12}$MDI | PTMO[a] | — | — |
| Biomer (Registered Trade Mark) | MDI | PTMO[a] | 1000 | Primarily EDA |

[a]poly(tetramethylene oxide)

Specimens shaped as dumbells were cut from the sheets and stretched over poly(methyl methacrylate) holders. This caused the central section to be strained to 250% of its original length. A polypropylene suture ligature was firmly tied around the centre of each specimen. This caused a localised increase in stress in the specimen. This test method provides a means for assessing the resistance to stress-induced biodegradation; the effect of stress on the acceleration of biodegradation is well established and is discussed in Szycher's review cited in the present application.

The specimens attached to their holders were sterilised with ethylene oxide and implanted into the subcutaneous adipose tissue in the dorsal thoraco-lumbar region of adult crossbred wether sheep.

After a period of three months the polyurethanes were retrieved. Attached tissue was carefully dissected away and the specimens were washed by soaking in 0.1M sodium hydroxide for 2 days at ambient temperature followed by rinsing in deionized water. The specimens were then dried in air and examined by SEM.

The specimens were ranked according to surface structure in the central straight region as determined by SEM as follows:

| Rank | Criteria |
|---|---|
| 1 | The specimen was smooth on all surfaces. |
| 2 | Small amounts of cracking or pitting were present adjacent to the ligature site. |
| 3 | Large amounts of cracking or pitting were present adjacent to the ligature site but no cracking or pitting was present elsewhere. |
| 4 | Large amounts of cracking or pitting were present adjacent to the ligature site and patches of stress cracks were present on the straight, central portion of the sample, remote from the ligature site. |
| 5 | Generalised stress cracking covered most or all of the central straight section of the sample. |

The rankings obtained were as follows.

TABLE 7

| Rank | Polyurethane |
|---|---|
| 1 | Example 4 |
| 1 | Example 5 |
| 1 | Example 6 |
| 1 | Example 8 |
| 4 | Tecoflex EG-80A (Registered Trade Mark) |
| 5 | Pellethane 2363-80A (Registered Trade Mark) |
| 5 | Biomer (Registered Trade Mark) |

TABLE 7-continued

| Rank | Polyurethane |
| --- | --- |
| 5 | Example 1 |

Control specimens, which were not implanted, but were cleaned with sodium hydroxide in an identical manner to those which had been explanted from sheep and control specimens which neither were implanted in sheep nor cleaned with sodium hydroxide were also examined by SEM. Both of these control groups showed no change in surface structure and were ranked 1 in all cases.

These results of these experiments show that the novel polyurethanes produced according to the present invention were of improved biostability when subjected to applied stress in vivo and would thus be suitable for use in implantable devices.

EXAMPLE 12

This example illustrates the use of bulk polymerization to prepare a polyurethane. The polymerization was carried out in a glass reaction vessel fitted with a mechanical stirrer, nitrogen bleed, and a condenser. Freshly distilled MDI (43.96 g, 0.176 mol) and poly(hexamethylene oxide)(Mn=690), (60.6 g, 0.087 mol) were placed in the vessel and heated to 80 C. for one hour under dry nitrogen. The prepolymer was allowed to cool to about 40 C. and then degassed under vacuum. 1,4-Butanediol (7.837 g) was added from a syringe and the mixture was stirred at high speed for 1 minute. Stannous octoate (0.01%, added as a 2.5% solution in toluene) was then added and stirring was continued for 30 seconds. The mixture was then poured onto a dish lined with teflon-coated cloth and cured in an oven at 100 C. for 15 hours under a flow of dry nitrogen. The cured polymer was melt pressed at 180 C. into 1 mm thick sheets and tested for mechanical properties. The results obtained are given in Table 8.

TABLE 8

| | Example 12 |
| --- | --- |
| Hardness, Shore A | 89 |
| Stress at 100% elongation, MPa | 11 |
| Stress at 300% elongation, MPa | 15.6 |
| Tensile strength, MPa | 15.9 |
| Elongation at break, % | 320 |
| Tensile set, % | 57 |
| Mn (daltons) | 59,200 |
| Dispersity (Mw/Mn) | 1.48 |

We claim:

1. A degradation resistant material which comprises a polyurethane or polyurethane-urea elastomeric composition which comprises a reaction product of:
(A) a soft segment macrodiol which is either:
(i) a homopolymer represented by formula I, $$HO-[(CH_2)_nO]_m-H \quad \quad I$$

wherein n represents an integer greater than 5 and less than 13, m is a number such that the number average molecular weight of the compound of formula I falls in the range from 218 to 5000 and optionally at least one hydrogen atom represented in formula I is substituted by a $C_1$ to $C_3$ alkyl group or a halogen atom;

(ii) a copolymer containing at least 25% by mass of repeating units $-(CH_2)_nO-$ wherein n is as defined in formula I above; or (iii) a mixture of macrodiols comprising greater than 10% of a macrodiol as defined in formula I above, with the proviso that the mixture of macrodiols does not include polyethylene glycol and/or polypropylene glycol;

(B) an aliphatic or aromatic diisocyanate; and
(C) optionally a chain extender.

2. A degradation resistant material according to claim 1, wherein the homopolymer (i) comprises a range of molecular weights such that the number average molecular weight falls between 218 and 5000.

3. A degradation resistant material according to claim 1, wherein the aliphatic or aromatic diisocyanate (B) is selected from the group consisting of:
4,4'-diphenylmethane diisocyanate (MDI);
methylene bis(cyclohexyl) diisocyanate ($H_{12}$MDI);
p-phenylene diisocyanate (p-PDI);
trans-cyclohexane-1,4-diisocyanate (CHDI);
1,6-diisocyanatohexane (DICH);
2,4-toluene diisocyanate (2,4-TDI);
meta-tetramethylxylene (m-TMXDI); and
para-tetramethylxylene diisocyanate (p-TMXDI).

4. A degradation resistant material according to claim 1, wherein the chain extender (C) is selected from the group consisting of:
1,4-butanediol (BDO);
1,6-hexanediol (HDO);
1,2-ethylene diamine (EDA);
1,6-hexanediamine (HDA); and
1,2-propanediamine (1,2-PDA).

5. A degradation resistant material according to claim 1, wherein the composition further comprises one or more of a cross-linking agent, a catalyst, an antioxidant, a stabilizer and a processing aid.

6. A material having improved durability in hostile environments which comprises a polyurethane or polyurethane-urea elastomeric composition as defined in claim 1.

7. A device or article which comprises a polyurethane or polyurethane-urea elastomeric composition as defined in claim 1.

8. A degradation resistant material according to claim 1, wherein the soft segment macrodiol is a homopolymer represented by formula I, $$HO-[(CH_2)_nO]_m-H \quad \quad I$$

wherein n represents an integer greater than 5 and less than 13, m is a number such that the number average molecular weight of the compound of formula I falls in the range from 218 to 5000 and optionally at least one hydrogen atom represented in formula I is substituted by a $C_1$ to $C_3$ alkyl group or a halogen atom.

9. A degradation resistant material according to claim 1 wherein the soft segment macrodiol is a copolymer containing at least 25% by mass of repeating units $-(CH_2)_nO-$ wherein n greater than 5 and less than 13.

10. A degradation resistant material according to claim 8 wherein n is 6, 8 or 10.

11. A degradation resistant material which comprises a polyurethane or polyurethane-urea elastomeric composition which comprises a reaction product of:
(A) a soft segment macrodiol which is either:
(i) a homopolymer represented by formula I,

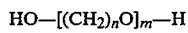

$$\text{HO}-[(\text{CH}_2)_n\text{O}]_m-\text{H} \quad \text{I}$$

wherein n represents an integer greater than 5 and less than 13, m is a number such that the number average molecular weight of the compound of formula I falls in the range from 218 to 5000 and at least one hydrogen atom represented in formula I is substituted by a halogen atom;
(ii) a copolymer containing at least 25% by mass of repeating units $-(\text{CH}_2)_n\text{O}-$ wherein n is as defined in formula I above; or
(iii) a mixture of macrodiols comprising greater than 10% of a macrodiol as defined in formula I above;

(B) an aliphatic or aromatic diisocyanate; and
(C) optionally a chain extender.

12. A degradation resistant material according to claim 11 wherein the halogen atom is fluorine.

13. An in vivo degradation resistant material which comprises a polyurethane or polyurethane-urea elastomeric composition which comprises a reaction product of:
(A) a soft segment macrodiol which is either:
(i) a homopolymer represented by formula I,

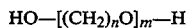

$$\text{HO}-[(\text{CH}_2)_n\text{O}]_m-\text{H} \quad \text{I}$$

wherein n represents an integer greater than 5 and less than 13, m is a number such that the number average molecular weight of the compound of formula I falls in the range from 218 to 5000 and optionally at least one hydrogen atom represented in formula 1 is substituted by a $C_1$ to $C_3$ alkyl group or a halogen atom;
(ii) a copolymer containing at least 25% by mass of repeating units $-(\text{CH}_2)_n\text{O}-$ wherein n is as defined in formula I above; or
(iii) a mixture of macrodiols comprising greater than 10% of a macrodiol as defined in formula I above;

(B) an aliphatic or aromatic diisocyanate; and
(C) optionally a chain extender.

14. A biomaterial which comprises a polyurethane or polyurethane-urea elastomeric composition as defined in claim 13.

15. Artificial leather, shoe soles or cable sheathing which comprises a polyurethane or polyurethane-urea elastomeric composition as defined in claim 13.

16. A medical device article or implant which comprises a polyurethane or polyurethane-urea elastomeric composition as defined in claim 13.

17. A medical device, article or implant according to claim 16 which is a pacemaker lead, a catheter, an implantable prosthesis, a cardiac assist device, a heart valve, a suture, a vascular graft, an extra-corporeal device or an artificial heart.

18. A medical device, article or implant according to claim 16 which is a pacemaker lead or a defibrillator lead.

19. A polyurethane or polyurethane urea elastomeric composition as defined in claim 13.

* * * * *